United States Patent
Riley et al.

(10) Patent No.: US 11,708,312 B2
(45) Date of Patent: Jul. 25, 2023

(54) EFFICIENT LOW-TEMPERATURE, CATALYST-FREE DEHYDROGENATION OF ALKANES

(71) Applicants: National Technology & Engineering Solutions of Sandia, LLC, Albuquerque, NM (US); UNM Rainforest Innovations, Albuquerque, NM (US)

(72) Inventors: Christopher Ryan Riley, Albuquerque, NM (US); Andrew De La Riva, Albuquerque, NM (US); Stanley Shihyao Chou, Albuquerque, NM (US); Abhaya Datye, Albuquerque, NM (US)

(73) Assignees: National Technology & Engineering Solutions of Sandia, LLC, Albuquerque, NM (US); UNM Rainforest Innovation, Albuquerque, NM (US)

( * ) Notice: Subject to any disclaimer, the term of this patent is extended or adjusted under 35 U.S.C. 154(b) by 0 days.

(21) Appl. No.: 17/864,808

(22) Filed: Jul. 14, 2022

(65) Prior Publication Data
US 2023/0037379 A1   Feb. 9, 2023

Related U.S. Application Data

(60) Provisional application No. 63/224,476, filed on Jul. 22, 2021.

(51) Int. Cl.
*C07C 5/327* (2006.01)

(52) U.S. Cl.
CPC .................................. *C07C 5/327* (2013.01)

(58) Field of Classification Search
CPC ..................................................... C07C 5/327
See application file for complete search history.

(56) References Cited

U.S. PATENT DOCUMENTS

| 2014/0335009 A1* | 11/2014 | Mordkovich | ........ B01J 19/2415 |
| | | | 423/447.3 |
| 2015/0209759 A1* | 7/2015 | Al-Hazmi | .............. B01J 23/626 |
| | | | 502/328 |

OTHER PUBLICATIONS

Rosli, M. N. and Aziz, N., "Simulation of Ethane Steam Cracking with Severity Evaluation," IOP Conference Series: Materials Science and Engineering, 2017, vol. 162, 012017, 6 pages.
(Continued)

*Primary Examiner* — Thuan D Dang
(74) *Attorney, Agent, or Firm* — Kevin W. Bieg (57) ABSTRACT

Steam cracking of ethane, a non-catalytic thermochemical process, remains the dominant means of ethylene production. The severe reaction conditions and energy expenditure involved in this process incentivize the search for alternative reaction pathways and reactor designs which maximize ethylene yield while minimizing cost and energy input. According to the present invention, ethylene yields as high as 68% were obtained with a quartz open tube reactor without the use of a catalyst or a cofed stream of oxidizing agents. The open tube reactor design promotes simplicity, (Continued)

low cost, and negligible coke formation. Reactor designs can be optimized to improve the conversion of ethane to ethylene via non-oxidative dehydrogenation, an approach which shows promise for decentralized production of ethylene from natural gas deposits.

6 Claims, 9 Drawing Sheets

(56) References Cited

OTHER PUBLICATIONS

Stangland, E. E., "Shale Gas Implications for $C_2$—$C_3$ Olefin Production: Incumbent and Future Technology," Annual Review of Chemical and Biomolecular Engineering, 2018, vol. 9, pp. 341-364.
Symoens, S. H. et al., "State-of-the-Art of Coke Formation during Steam Cracking: Anti-Coking Surface Technologies," Industrial and Engineering Chemistry Research, 2018, vol. 57, pp. 16117-16136.
Li, X. et al., "Improved Catalytic Performance of Ethane Dehydrogenation in the Presence of $CO_2$ over Zr-Promoted $Cr/SiO_2$," ACS Omega, 2019, vol. 4, pp. 22562-22573.
Theofanidis, S. A. et al., "$CO_2$-Oxidative Ethane Dehydrogenation over Highly Efficient Carbon-Resistant Fe-Catalysts," Journal of Catalysis, 2020, vol. 388, pp. 52-65.
Cheng, Y., "Chromium-Based Catalysts for Ethane Dehydrogenation: Effect of SBA-15 Support," Microporous and Mesoporous Materials, 2016, vol. 234, pp. 370-376.
Keller, G. E. and Bhasin, M. M., "Synthesis of Ethylene via Oxidative Coupling of Methane," Journal of Catalysis, 1982, vol. 73, pp. 9-19.
Al-Mamoori, A. et al., "Oxidative Dehydrogenation of Ethane to Ethylene in an Integrated $CO_2$ Capture-Utilization Process," Applied Catalysis B: Environmental, 2020, vol. 278, 119329, 10 pages.
Seki, H. et al., "Effect of Ba Addition to Ga-α-$Al_2O_3$ Catalyst on Structure and Catalytic Selectivity for Dehydrogenation of Ethane," Applied Catalysis A, General, 2019, vol. 581, pp. 23-30.
Ding, W. et al., "Alkali-Metal Enhanced $LaMnO_3$ Perovskite Oxides for Chemical Looping Oxidative Dehydrogenation of Ethane," Applied Catalysis A, General, 2021, vol. 609, 117910., 8 pages.
Gaffney, A. M. and Manson, O. M., "Ethylene Production via Oxidative Dehydrogenation of Ethane using M1 Catalyst," Catalysis Today, 2017, vol. 285, pp. 159-165.
Liu, C. J. et al., "Phase Transformation of Nb in Carburized Zone of 25Cr35NiNb+MA Alloy after Service," Procedia Engineering, 2015, vol. 130, pp. 693-700.
Sarris, S. A. et al., "Alumina-based Coating for Coke Reduction in Steam Crackers," Materials, 2020, vol. 13, 2025, 19 pages.
Xu, C. et al., "Kinetic Modeling of Ethane Pyrolysis at High Conversion," The Journal of Physical Chemistry A, 2011, vol. 115, pp. 10470-10490.
Heracleous, E. and Lemonidou, A. A., "Homogeneous and Heterogeneous Pathways of Ethane Oxidative and Non-Oxidative Dehydrogenation Studied by Temperature-Programmed Reaction," Applied Catalysis A: General, 2004, vol. 269, pp. 123-135.

\* cited by examiner

EFFICIENT LOW-TEMPERATURE, CATALYST-FREE DEHYDROGENATION OF ALKANES

CROSS-REFERENCE TO RELATED APPLICATION

This application claims the benefit of U.S. Provisional Application No. 63/224,476, filed Jul. 22, 2021, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

STATEMENT REGARDING PRIOR DISCLOSURES BY THE INVENTOR OR A JOINT INVENTOR

The following disclosure is submitted under 35 U.S.C. 102(b)(1)(A): Christopher R. Riley, Andrew De La Riva, Isabel L. Ibarra, Abhaya K. Datye, and Stanley S. Chou, "Achieving high ethylene yield in non-oxidative ethane dehydrogenation," *Applied Catalysis A: General* 624, 118309 (2021). The subject matter of this disclosure was conceived of or invented by the inventors named in this application.

FIELD OF THE INVENTION

The present invention relates to the production of alkenes via the efficient, low-temperature, catalyst-free dehydrogenation of alkanes in a tube reactor.

BACKGROUND OF THE INVENTION

Industrial steam cracking of ethane and naptha is the dominant means of ethylene production, yielding over 150 million tons of ethylene per year globally. High production volume is required to meet the growing demand for ethylene, which serves as a crucial polymer and petrochemical precursor. See I. Amghizar et al., *Engineering* 3(2), 171 (2017). Although steam cracking operations are highly optimized, the process consumes significant energy (16 GJ/ton ethylene) and generates large quantities of $CO_2$ (approximately 1 ton $CO_2$/ton ethylene). See T. Ren et al., *Energy* 33, 817 (2008). Steam cracking reactors are operated at extreme temperatures, typically between 850-950° C., to raise the equilibrium conversion of ethane to ethylene, given the high endothermicity of this reaction. See M. N. Rosli and N. Aziz, *IOP Conf. Ser.: Mater. Sci. Eng.* 162, 012017 (2017). Ethylene yield benchmarks are approximately 55%. See E. E. Stangland, Annu. Rev. Chem. *Biomol. Eng.* 9, 341 (2018). Co-fed steam reduces coke formation but adds significantly to the energy required to heat reactant streams and creates a corrosive environment within cracking reactors, lowering the lifespan of system components. See S. H. Symoens et al., *Ind. Eng. Chem. Res.* 57, 16117 (2018). These severe operational conditions have generated interest in developing alternative means of ethylene production, with focus placed on maximizing ethylene yield while minimizing energy input, operational costs, and capital investment. Decentralized production of ethylene from natural gas, which contains relatively dilute ethane concentrations (between 0-25%), is one potential approach. Such operations would require simplified reactor designs and milder operating conditions without sacrificing ethylene yield.

Because steam cracking is a noncatalytic thermochemical process, catalyzed reactions have received significant attention as alternative means of ethylene production. See I. Amghizar et al., *Engineering* 3(2), 171 (2017). Catalyzed ethane dehydrogenation is a viable option, which can be performed under both oxidative and non-oxidative conditions. Co-feeding oxidizing agents, such as $O_2$ or $CO_2$, lowers reaction endothermicity through creation of oxidized byproducts, like $H_2O$, mitigating thermodynamic constraints and allowing appreciable alkane conversion at lower reaction temperatures. See X. Li et al., *ACS Omega* 4, 22562 (2019); S. A. Theofanidis et al., *J. Catal.* 388, 52 (2020); Y. Cheng et al., *Micropor. Mesopor. Mat.* 234, 370 (2016); G. E. Keller and M. M. Bhasin, *J. Catal.* 73, 9 (1982); A. Al-Mamoori et al., *Appl. Catal. B* 278(5), 119329 (2020); H. Seki et al., *Appl. Catal. A* 581, 23 (2019); and W. Ding et al., *Appl. Catal. A* 609, 117910 (2021). However, total oxidation of hydrocarbon reactants and formation of unwanted products is highly exothermic and thermodynamically favored. Catalytic oxidative dehydrogenation of ethane has achieved ethylene selectivity and yields better than steam cracking. See A. M. Gaffney and O. M. Mason, *Catal. Today* 285, 159 (2017). However, several studies do report excellent ethylene yield at the beginning of the reaction, followed by rapid deactivation. See X. Li et al., *ACS Omega* 4, 22562 (2019); S. Wang et al., *Chem. Eng. Technol.* 23, 1099 (2000); and A. S. Al-Awadi et al., *Catalysts* 10(1), 97 (2020). A wide variety of molten salts and complex reducible oxide catalysts are studied for this reaction, which are based on chromia (as used industrially in the Catofin process), zirconia, niobia, molybdenum, and iron oxide constituents. See C. P. Kumar et al., *Top. Catal.* 50, 156 (2008); Y. Gao et al., *Sci. Adv.* 6(17), eaaz9339 (2020); X. Li et al., *ACS Omega* 4, 22562 (2019); Y. Cheng et al., *Micropor. Mesopor. Mat.* 234, 370 (2016); G. E. Keller and M. M. Bhasin, *J. Catal.* 73, 9 (1982); A. Al-Amoori et al., *Appl. Catal. B* 278(5), 119329 (2020); A. S. Al-Awadi et al., *Catalysts* 10(1), 97 (2020); A. Talati et al., Adv. Powder Technol. 27, 1195 (2016). S. A. Theofanidis et al., *J. Catal.* 388, 52 (2020); S. Wang et al., *Chem. Eng. Technol.* 23, 1099 (2000); M. L. Rodriguez et al., *Ind. Eng. Chem. Res.* 50, 2690 (2010); Y. S. Al-Zeghayer et al., *J. King Saud Univ. Eng. Sci.* 22, 21 (2010); Y. S. Yun et al., *Appl. Catal. B* 237, 554 (2018); D. Melzer et al., *Nat. Commun.* 10, 4012 (2019); K. Takanabe and S. Shahid, AIChE J. 63(1), 105 (2016); E. Heracleous and A. A. Lemonidou, *Appl. Catal. A* 269, 123 (2004); C. Xin et al., *Appl. Catal. A* 610, 117946 (2021); Z. Yang et al., *J. Am. Chem. Soc.* 142(38), 16429 (2020); L.-C. Wang et al., *Appl. Catal. B* 256, 117816 (2019); M. H. Jeong et al., *Appl. Catal. B* 270, 118887 (2020); and S. Yusuf et al., *Appl. Catal. B* 257, 117885 (2019). Despite the significant cost, platinum-based catalysts are often chosen to facilitate non-oxidative dehydrogenation of ethane. Indeed, the industrial Olexflex process for dehydrogenation of propane utilizes Pt—Sn bimetallic catalysts. See J. J. H. B. Sattler et al., *Chem. Rev.* 114, 10613 (2014). Other Pt bimetallics have been investigated in the literature for ethane dehydrogenation with the general finding that alloying Pt reduces coke formation, increases ethylene selectivity, and improves Pt dispersion. See Z. Wu et al., *J. Am. Chem. Soc.* 140, 14870 (2018); E. C. Wegener et al., *Catal. Today* 299, 146 (2018); Q. Zhang et al., *J. Catal.* 368, 79 (2018); V. J. Cybulskis et al., *ACS Catal.* 7, 4173 (2016); Z. Yu et al., *AIChE J.* 61, 4367 (2015); and V. Galvita et al., *J. Catal.* 271, 209 (2010).

Compared to propane dehydrogenation, operational temperatures must be higher during ethane dehydrogenation to overcome increased reaction endothermicity. Previous studies have tested Pt intermetallic catalysts within the temperature range of 500-750° C., with varying degrees of catalyst deactivation observed. See E. C. Wegener et al., *Catal. Today* 299, 146 (2018); Q. Zhang et al., *J. Catal.* 368, 79 (2018); V. J. Cybulskis et al., *ACS Catal.* 7, 4173 (2016); Z. Yu et al., *AIChE J.* 61, 4367 (2015); V. Galvita et al., *J. Catal.* 271, 209 (2010); and Z. Wu et al., *J. Am. Chem. Soc.* 140, 14870 (2018). Thus, the thermal stability of such catalysts applied in ethane dehydrogenation reaction is of particular concern.

The severe operational conditions involved in ethane dehydrogenation can be mitigated through novel reactor designs. Hydrogen-permeable membranes can increase equilibrium conversion of ethane. However, membranes add significantly to system cost, and require a sweep gas, which complicates system operation. See E. Gobina et al., *Chem. Eng. Sci.* 50, 2311 (1995); S. Dangwal et al., Chem. Eng. J. (Lausanne) 328, 862 (2017); A. M. Avila et al., *Micropor. Mesopor. Mat.* 190, 301 (2014); and A. M. Champagnie et al., *J. Catal.* 134, 713 (1991). Metallurgical improvements have allowed steel steam cracking furnace components to withstand higher operational temperatures, enabling high ethane conversion. See S. H. Symoens et al., *Ind. Eng. Chem. Res.* 57, 16117 (2018). The influence of temperature, alloying elements, and co-fed steam have been thoroughly investigated to manage ethylene yield, coke formation, and reactor lifespan. Addition of nickel and niobium alloying elements to steel cracking furnaces improved thermal stability, but these inclusions promote coke formation and maintenance requirements. See S. H. Symoens et al., *Ind. Eng. Chem. Res.* 57, 16117 (2018); and C. J. Liu et al., *Procedia Eng.* 130, 693 (2015). Accumulation of coke restricts gas flow within the furnace and leads to carburization of steels, which structurally degrades cracking furnace components. Alternative reactor wall materials and coatings made of alumina, silicon carbide, or quartz are proposed as potential replacements. See S. H. Symoens et al., *Ind. Eng. Chem. Res.* 57, 16117 (2018); and S. A. Sarris et al., *Materials* 13, 2025 (2020). Previous work shows that thermal reactions conducted in the gas phase are quite selective for the dehydrogenation of ethane to ethylene, because the activation barrier for the abstraction of a hydrogen atom from ethylene (461 KJ/mol) is higher than that for abstraction of hydrogen from ethane (410 KJ/mol). See A. M. Dean, *J. Phys. Chem.* 89, 4600 (1985). On the contrary, olefins are much more reactive than alkanes on solid surfaces, and especially on Pt-based catalysts, leading to coke formation. Hence, the contribution of thermal reactions to ethane dehydrogenation at the lower temperatures where catalytic reactions are studied needs further investigation. Heracleous et al. studied oxidative and non-oxidative dehydrogenation of ethane in an empty tube and with a 20 wt % Mo/$Al_2O_3$ catalyst. See E. Heracleous and A. A. Lemonidou, *Appl. Catal. A* 269, 123 (2004). They reported that the presence of oxygen was beneficial for ethane conversion even for the homogeneous reaction carried out in an empty tube. A similar yield of ethylene was reported for oxidative dehydrogenation at 700° C. for the homogeneous and the catalyzed reaction (approximately 56% with a 2% ethane feed). For the non-oxidative dehydrogenation, they reported significant coke formation with a $H_2/C_2H_4$ ratio greater than 1 for the empty tube. On the other hand, Xu et al. reported excellent selectivity to ethylene in an empty quartz tube reactor at 700° C. See C. Xu et al., *J. Phys. Chem. A* 115, 10470 (2011). Some of these differences in coke formation and selectivity may be a result of the reactor wall composition and the influence of the solid phase (catalyst or catalyst support).

SUMMARY OF THE INVENTION

The present invention is directed to a tube reactor for the dehydrogenation of an alkane, comprising an open quartz tube, and a furnace to heat the open quartz tube to a reactor temperature of between 575° C. and 750° C. The invention is further directed to a method for dehydrogenation of an alkane, comprising providing a tube reactor comprising an open quartz tube, and a furnace to heat the open quartz tube; heating the open quartz tube to a reactor temperature of between 575° C. and 750° C.; and introducing a feed gas comprising an alkane into the heated open quartz tube, whereby the alkane is at least partially converted into an alkene. As an example, the method can efficiently convert ethane into ethylene without the need for a catalyst or cofed streams of oxidizing agents.

Thermal, gas phase reactions dominate the ethane dehydrogenation reaction performed at high temperature (700° C.). A hollow quartz tube that was pristine and free of defects led to superior performance compared to a reactor packed with inert solids or even state-of-the-art Pt-based catalysts. At elevated temperatures, Pt-based catalysts showed rapid deactivation due to coke deposition and some sintering. In contrast, the open tube reactor continued to perform with no apparent deactivation and minimal coke formation. The reactor geometry can be further optimized to achieve better heat integration and to quench any undesirable free radical reactions. Such modular reactor designs may be suitable for conversion of distributed ethane resources available through fracking. Fracking-derived natural gas typically contains ethane concentrations ranging between 0-25%. Regardless of ethane concentration, the open tube quartz reactor consistently out-performed packed bed reactors. The presence of any solid within the reactor, even an active catalyst, had a negative effect on overall ethylene yield at the highest temperatures of operation. Thus, quartz represents a viable reactor material that does not cause significant coking or suffer from carburization-induced degradation as seen in conventional steam cracking furnaces.

BRIEF DESCRIPTION OF THE DRAWINGS

The detailed description will refer to the following drawings, wherein like elements are referred to by like numbers.

DETAILED DESCRIPTION OF THE INVENTION

The present invention is directed to a tube reactor that can convert alkanes to alkenes with high yields without addition of a catalyst or co-fed steam or $H_2$, meeting or exceeding benchmarks from steam cracking. For example, using a feed gas consisting of 2.5-25% ethane in nitrogen (consistent with ethane concentrations in natural gas deposits), a yield of 67% ethylene at a maximum reactor temperature near 750° C. was achieved. Careful preparation of reactor walls allows for negligible coke formation. Without the use of a catalyst or concern for coke formation, an open tube reactor demonstrates stable performance without any deactivation or the need for regeneration. A quartz tube reactor is not prone to carburization, which degrades conventional cracking furnace components. Pt-based catalysts are effective at low temperatures, such as 600° C. However, the performance of these catalysts deteriorates when operated at temperatures of 700° C. and higher. A simple open tube quartz reactor design that quenches the products and allows better heat integration can provide an alternative to the capital-intensive steam cracking process for distributed manufacturing of ethylene from shale gas.

As an example, multiple tube reactor configurations were tested to evaluate ethane dehydrogenation reactivity, including hollow open tube, annular, and packed beds containing catalysts as well as inert materials. Inert materials were tested to determine any beneficial effects in terms of initiating thermochemically-induced free radical reactions and low activity for ethylene hydrogenation or undesired coke formation at high temperatures, which may lower the yield. The reactor tubes preferably have a circular cross-section for ease of manufacture and less likelihood of coke formation at corners. However, other tube cross sections (e.g., square, rectangular) can also be used. The exemplary reactor tubes were made of fused silica quartz (4 mm ID and 6 mm OD), 316 L stainless-steel (3.5 mm ID and 6.35 mm OD), and alumina (4.75 mm ID and 6.35 mm OD with 99.5% purity). An Inconel wire and quartz rods were fitted within the quartz tube to create annular reactor configurations. A $PtSn_x/Al_2O_3$ (nominal 0.5 wt % Pt) was obtained from a commercial supplier. A $PtMn_x/SiO_2$ catalyst (nominal 2 wt % Pt) was synthesized using the method described by Wu et al. through sequential incipient wetness impregnation of pH-adjusted aqueous solutions of manganese (II) nitrate tetrahydrate and tetraamine platinum (II) nitrate onto silica gel (200-425 mesh size, grade 643). See Z. Wu et al., *J. Am. Chem. Soc.* 140, 14870 (2018). The sample was dried under ambient conditions, calcined at 550° C., and then reduced for 30 minutes at 550° C. in a 50 ml/min flow of 10% hydrogen, balance nitrogen. The two platinum-containing catalysts are herein labeled "PtMn" and "PtSn". Packed beds of 20 mg of catalyst were loaded upstream of a quartz wool plug situated in the hottest region of the reactor. Inert materials were loaded in the same fashion but were placed both in the hottest region of the reactor and downstream of the heated region during separate tests. The label "Downstream" or "DS" designates this latter sample location where applicable.

Figure 1A:
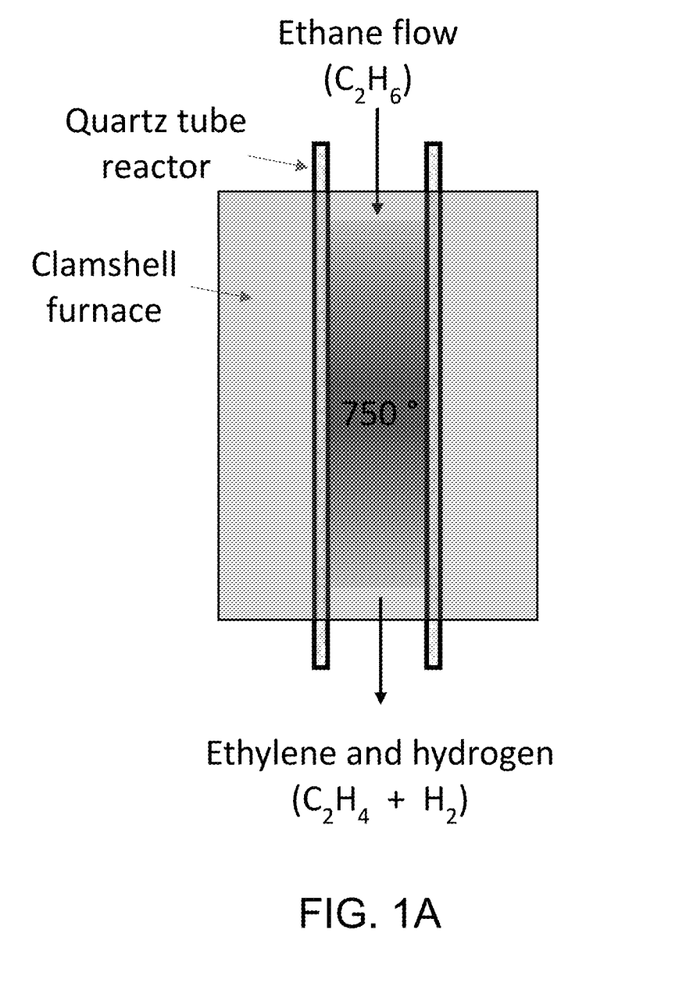
FIG. 1A is a schematic illustration of an open tube quartz reactor.
Figure 1B:
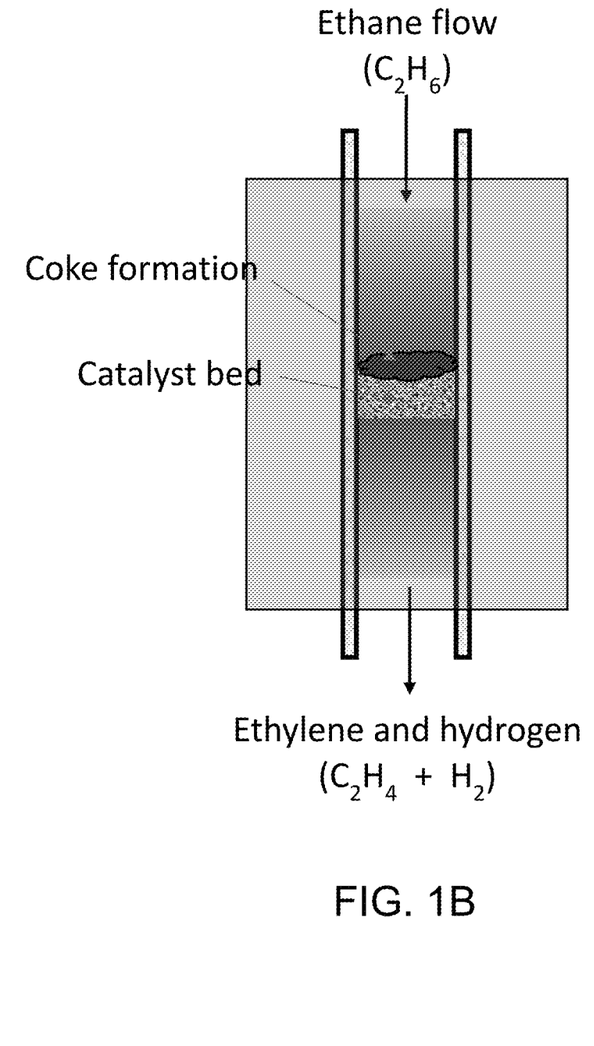
FIG. 1B is a schematic illustration of a packed bed tube reactor.

FIGS. 1A and 1B illustrate an open tube reactor and a packed bed tube reactor, respectively. The tube reactors were fitted within a vertically mounted clam-shell furnace with a heated chamber 10 inches in length. During reactions, feed gas was directed downward through the reactor. Temperature was measured with a K-type thermocouple built into the furnace, which was external to the reactor tubes. This external temperature was related to the temperature within the reactor tubes by feeding a K-type thermocouple into the open reactor tubes in one-inch increments under flowing nitrogen to gather temperature profiles prior to ethane reaction experiments. Temperature profiles were used to calculate kinetically averaged residence times for ethane reactant within the open-tube quartz, alumina, and stainless-steel reactors. Dehydrogenation of ethane was performed with feed gas compositions of 2.5, 5, 10, and 25% ethane in nitrogen with a total flow of 20 ml/min with furnace temperatures set from 575-700° C. in increments of 25° C. and pressure of approximately 0.8 atm (atmospheric pressure in Albuquerque, N. Mex.). Effluent gas composition was measured with a gas chromatograph (GC) equipped with a flame ionization detector (FID) and a micro GC equipped with a thermal conductivity detector (TCD). Ethane conversion ($X_{ethane}$), ethylene selectivity ($S_{ethylene}$), and ethylene yield ($Y_{ethylene}$) were calculated as follows:

$$X_{ethane} = \frac{(C_2H_{6in})/N_{2in} - (C_2H_{6out})/N_{2out}}{(C_2H_{6in})/N_{2in}} * 100\%$$

$$S_{ethylene} = \frac{C_2H_{4out}/N_{2out}}{(C_2H_{6in})/N_{2in} - (C_2H_{6out})/N_{2out}} * 100\%$$

$$Y_{ethylene} = X_{ethane} * S_{ethylene}$$

Area counts generated from the GC FID signal were used to determine ethane and ethylene concentrations entering and exiting the reactors, since these counts are proportional to the concentration of those gaseous species. The nitrogen concentration in the gas flowing in and out of reactor (measured via TCD) was used as an internal standard to correct for the change in total moles of gas resulting from the dehydrogenation reaction. Since the molar flow rate of $N_2$ through the reactor remains unchanged, the $N_2$ counts cancel out of this equation providing a correction for the change in volume due to reaction. Similarly, the total GC FID area of the detected hydrocarbons allows the determination of a carbon balance. In these experiments, formation of coke was observed only in a few cases, generally when a catalyst was used. Coke formation was measured via several methods.

Carbon analysis was conducted on spent Pt catalysts to quantify coke formation using an elemental analyzer. Recovered samples were combusted at 980° C. Carbon dioxide produced was separated via gas chromatography and detected using a mass spectrometer. Following an isothermal reaction at a furnace temperature of 700° C. for 4 hours in 5% ethane, the quartz tube with and without addition of quartz wool and $PtMn_x$—$SiO_2$ and $PtSn_x$—$Al_2O_3$ catalysts was also visually inspected for coke deposits.

Physical characterization of the solids whose reactivity for ethane dehydrogenation was compared to that of an open tube reactor was conducted. As measured by X-ray fluorescence (XRF), Pt content in PtSn and PtMn catalysts was 0.4 and 1.8 wt %, respectively, which is near the nominal loadings of 0.5 and 2 wt %. Ceria-zirconia contained 6.9 at % zirconium dopant. Composition and surface area for the select samples are listed in Table 1. Transmission electron microscopy (TEM) images of Pt-containing catalysts show metallic particles several nanometers in diameter. Crystalline phases of ceria-zirconia, alumina, and quartz powders were confirmed via X-ray diffraction (XRD) analysis. Prior to running reactions with these materials, temperature profiles were measured in the quartz, alumina, and stainless-steel reactors while flowing nitrogen through each. The temperatures within each reactor were measured in 1-inch segments along the 10-inch heated region of the reactor and referenced to a thermocouple built into the furnace but external to the reactor. These profiles show that the actual temperatures within the open tube reactors were, at highest, approximately 50° C. greater than the temperature recorded by the furnace thermocouple. For simplicity, data are presented as a function of the built-in furnace thermocouple temperature, which is referred to herein as the operating temperature.

TABLE 1

XRF compositional results and Brunauer-Emmett-Teller (BET) surface area measurements of packed bed materials.

| Sample | Composition (wt %) | | | Specific surface area (m²/g) |
| --- | --- | --- | --- | --- |
| | Pt | Sn | Mn | |
| $PtSn_x$ – $Al_2O_3$ | 0.4 | 3.3 | — | 196 |
| $PtMn_x$ – $SiO_2$ | 1.8 | — | 4.9 | 256 |
| SBa 200 $Al_2O_3$ | — | — | — | 187 |
| Quartz sand | — | — | — | 0.2 |
| Quartz wool | — | — | — | 1.7 |

| Sample | Composition (at %) | |
| --- | --- | --- |
| | Ce | Zr |
| $Ce_{1-x}Zr_xO_{2-y}$ | 93.1 | 6.9 |

Figure 2A:
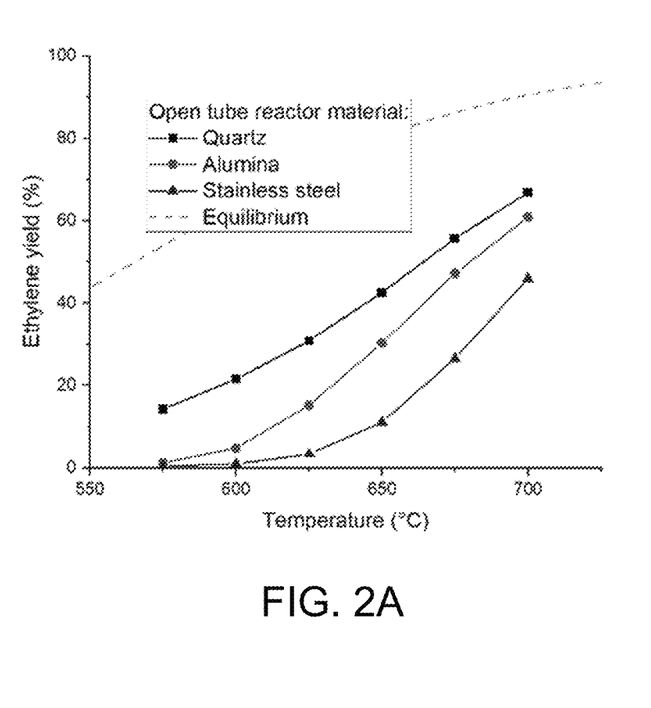
FIG. 2A is a graph of ethylene yield as a function of temperature for 5% ethane in nitrogen gas fed into open tube reactors.
Figure 2B:
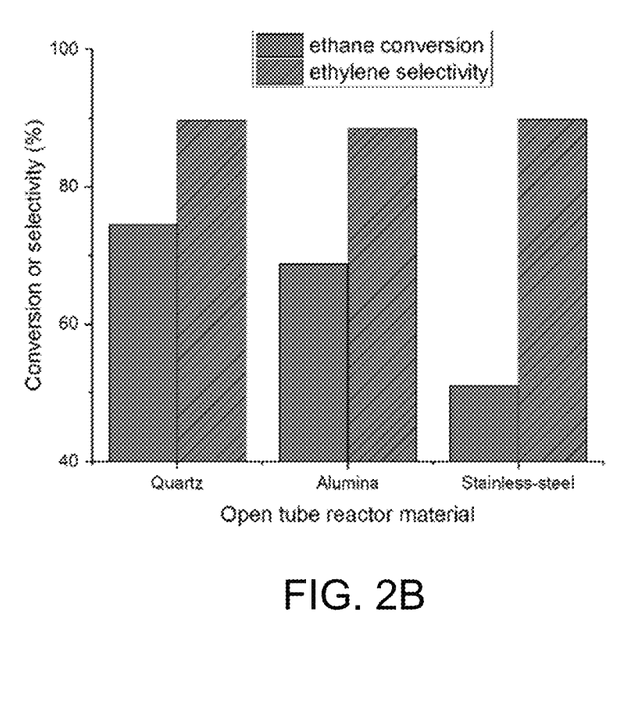
FIG. 2B is graph of ethylene selectivity and ethane conversions at a temperature of 700° C. for the open tube reactors.

Ethane dehydrogenation was conducted first using open-tube reactors with 5% ethane feed in nitrogen and 20 ml/min total flow. As shown in FIG. 2A, these results demonstrate that ethylene yield is influenced by the reactor tube material and that the quartz tube provides the highest yield. Ethane conversion and ethylene selectivity values for the reactor tubes at 700° C. are shown in FIG. 2B. Among the three open tube reactors, selectivity to ethylene at the 700° C. operating temperature tested is relatively similar, near 90%, suggesting that the same reaction pathway exists in each reactor. In the absence of a catalyst, reaction within the open tubes is presumed to initiate via thermally-generated methyl free radicals. See E. Heracleous and A. A. Lemonidou, *Appl. Catal. A* 269, 123 (2004). Ethane conversion, on the other hand, is lower when using the stainless-steel and alumina tubes, leading to the lower ethylene yield. The maximum temperature within each reactor was similar, particularly at the highest set furnace temperature of 700° C., but there were differences in the temperature profile, with a faster fall off in temperature toward each end of the heated region for the alumina and stainless-steel reactors. Since the reactor inner diameters were not identical, this can result in differing residence times for the gas molecules. Thus, a careful analysis of the residence time was performed by considering the variation in temperature along the axial direction. Kinetically averaged residence times were calculated based on the work of Fagley. See J. C. Fagley, *Ind. Eng. Chem. Res.* 31, 58 (1992). Table 2 lists the calculated residence time ($\tau$), considering the variation in temperature in the axial direction, and kinetically weighted average residence time ($\tau_{KA}$) for each of the open tube reactor types and the quartz rod annular reactor. The term $\exp(-E_a/RT)$ was used as a weighting factor normalized to the average temperature in each reactor. Examination of residence times at the highest operating temperature of 700° C. suggests that the overall conversion does not directly depend on the residence time, and the tube with the longest residence time does not achieve the highest conversion. This is because of the low flow rate and natural convection in the vertical tube leads to back mixing. This complex flow pattern implies that the calculated residence time based on plug flow is only an approximation. Therefore, the different performance of the three tubes may be ascribed to differences in surface temperature of the reactor wall, since the reactions are likely initiated in the gas phase in contact with the tube wall. As seen from the measured temperature profiles, the alumina and stainless-steel tubes show a more rapid fall off in temperature towards the end of the heated zone, while the quartz tube shows a higher temperature, likely due to differences in thermal conductivity. A complete explanation of the different performance of these tubes would require a CFD model coupled with gas phase kinetics.

TABLE 2

Computed residence times and conversion at an operating temperature of 700° C.

| Reactor tube | ID (mm) | OD (mm) | $\tau$ (s) | $\tau_{KA}$ (s) | $X_{ethane}$ at 700° C. (%) |
| --- | --- | --- | --- | --- | --- |
| Alumina | 4.50 | 6.35 | 4.02 | 3.57 | 68.7 |
| Quartz | 4.00 | 6.00 | 3.07 | 2.82 | 74.5 |
| Quartz (rod) | 4.00 (2.00)* | 6.00 | 2.30 | 2.12 | 75.1 |
| SS | 3.50 | 6.35 | 2.40 | 2.17 | 51.1 |

*Quartz tube reactor (ID 4 mm) with an annular quartz rod (OD 2 mm) inserted through the whole length of the heated zone to create an annular flow pattern.

Table 3 lists the concentration of significant gaseous reactants, products, and inerts detected via GC measurement during reactions with the open tube reactors. Methane is the dominant undesired gaseous product of ethane dehydrogenation within each open tube reactor. However, methane remains a very minor product, even at the highest temperatures tested. Molar ratios of $H_2/C_2H_4$ remain close to unity for the open tube reactors as evident from the concentration ratios, which confirms the high selectivity toward ethylene and negligible coke formation. These results agree with those in a study by Xu et al., who found similar product distribution trends and $H_2/C_2H_4$ ratios near unity when conducting ethane pyrolysis in a quartz tube reactor, which held for 50% ethane feed and temperatures higher than those used in this present study. See C. Xu et al., *J. Phys. Chem. A* 115, 10470 (2011). The reported energy barrier for activation of C—H bonds is higher for ethylene than for ethane, which contributes to the selectivity of the thermal dehydrogenation reaction in the absence of an oxidizing agent. See E. Heracleous and A. A. Lemonidou, *Appl. Catal. A* 269, 123 (2004); and A. M. Dean, *J. Phys. Chem.* 89, 4600 (1985). Materials such as iron and nickel within steel steam cracking coils are known to catalyze coke formation, particularly during start up. Taniewski et al. reported decomposition of ethylene within a stainless-steel tube reactor into carbon, methane, and hydrogen during ethane pyrolysis. See M. Taniewski et al., *Catal. Today* 13, 529 (1992). On the other hand, the authors note the relative stability within a silica reactor. Carbon mass balances were computed through gas chromatograph measurements of the gas compositions entering and exiting the reactors, which are also listed in Table 3. Approximately 95-100% of the carbon entering the reactor tubes as ethane is accounted for as methane, ethylene, ethane, propane, and propene exiting each reactor. Previous studies of ethane pyrolysis within inert tube reactors detected additional gaseous products, including acetylene, benzene, 1,3-butadiene, n-butane, toluene, 1-butene, and allene. See M. H. Saldana et al., *Energ. Fuels* 30, 9703 (2016). These were not detected in the present experiments, likely due to very low concentrations, which may account for the discrepancy in the carbon balances listed. The low concentrations of ethane limit the accuracy of TCD measurements, and the GC analysis using the FID detector did not detect hydrocarbons beyond $C_1$-$C_3$.

Figure 2C:
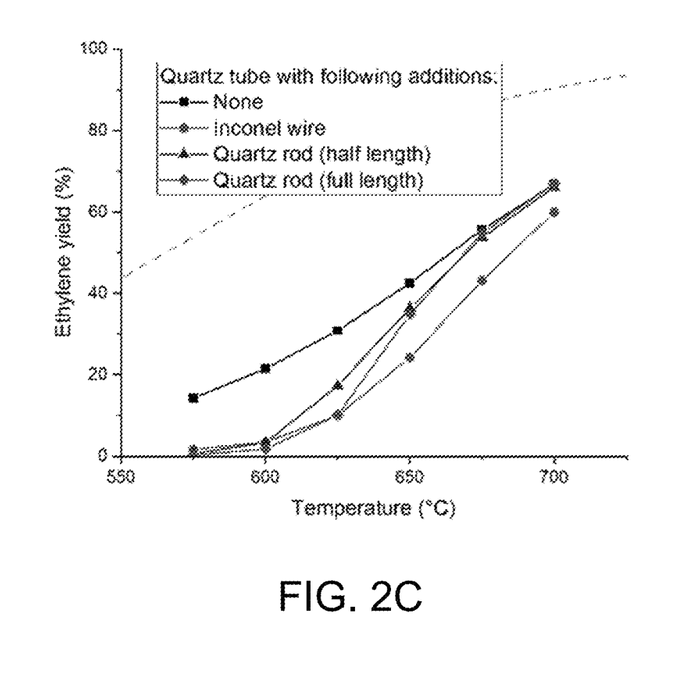
FIG. 2C is a graph of ethylene yield as a function of temperature for 5% ethane in nitrogen gas fed into quartz tube reactors with annular Inconel wire and quartz rods placed within the reactor.
Figure 2D:
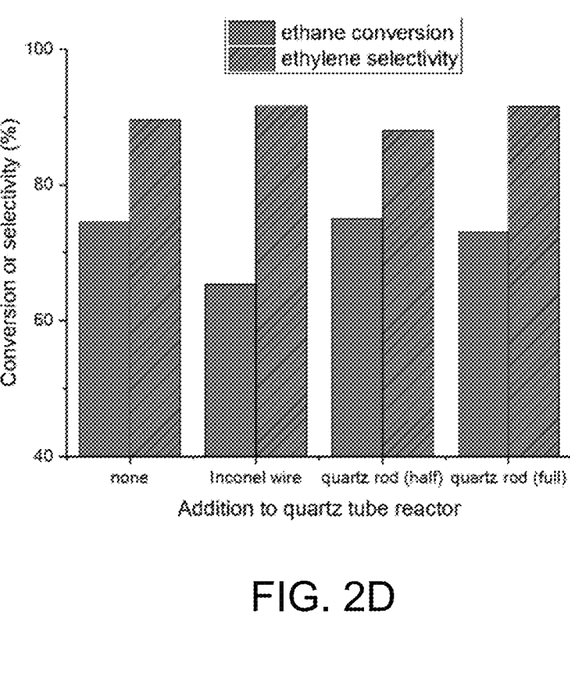
FIG. 2D is graph of ethylene selectivity and ethane conversions at a temperature of 700° C. for the annular tube reactors.

Since the open quartz tube showed the highest yield for ethylene, an annular flow geometry within the quartz tube reactor may be beneficial by changing gas flow dynamics. An annular reactor geometry was accomplished by adding either an Inconel wire or a quartz rod to the center of the open quartz tube. The quartz rod was axially positioned either within the entire heated region (labeled as "full length") or within the downstream half of the heated region ("half length") of the reactor tube on separate tests. Results from the annular tube reactor experiments are shown in FIGS. 2C and 2D. Ethylene yield remained highest in the open tube quartz reactor over nearly the whole temperature range tested. At a set temperature of 700° C., however, the yield is nearly identical in the quartz tube with and without the annular quartz rod, regardless of rod positioning. Ethylene yield at 700° C. ranged from 66.8-66.9% between the open quartz tube with and without inclusion of the annular quartz tube positioned through the entire length of the heated reactor region. The annular quartz rod increased decreased the reactor volume by 25% and changed the effective residence time from 3.07 to 2.30 seconds. The difference in effective residence time caused by varying dimensions between the open quartz, alumina, and stainless-steel reactor tubes is approximately 25% relative to the quartz tube. Because the ethylene yield essentially did not change with residence time in the quartz tube reactor configuration, the variations in yield between open tube reactor materials could be a result of the different heat transfer characteristics of quartz, alumina, and stainless steel. Below 675° C., addition of the quartz rod lowered ethylene yield, potentially by slowing heat transfer and leaving the annular quartz rod

TABLE 3

Gaseous products measured in mole percent as a function of temperature from reaction of 5% ethane feed gas in open tube reactors.

Quartz tube

| Temp (° C.) | $H_2$ (mol %) | $N_2$ (mol %) | $CH_4$ (mol %) | $C_2H_6$ (mol %) | $C_2H_4$ (mol %) | $C_3H_8$ (mol %) | $C_3H_6$ (mol %) | $X_{C_2H_6}$ (%) | $S_{C_2H_4}$ (%) | $Y_{C_2H_4}$ (%) | C balance (%) |
|---|---|---|---|---|---|---|---|---|---|---|---|
| 575 | 0.47 | 94.42 | 0.01 | 4.37 | 0.73 | 0.00 | 0.00 | 14.5 | 98.3 | 14.2 | 100 |
| 600 | 0.82 | 93.94 | 0.01 | 4.09 | 1.13 | 0.00 | 0.00 | 21.9 | 98.3 | 21.5 | 100 |
| 625 | 1.27 | 93.50 | 0.02 | 3.57 | 1.62 | 0.00 | 0.01 | 32.2 | 95.8 | 30.8 | 99 |
| 650 | 1.90 | 92.94 | 0.03 | 2.91 | 2.21 | 0.00 | 0.01 | 44.1 | 96.4 | 42.5 | 99 |
| 675 | 2.66 | 92.29 | 0.06 | 2.10 | 2.87 | 0.00 | 0.01 | 59.4 | 93.7 | 55.7 | 98 |
| 700 | 3.47 | 91.61 | 0.11 | 1.32 | 3.47 | 0.00 | 0.02 | 74.5 | 89.7 | 66.8 | 95 |
| bypass | 0.02 | 94.48 | 0.00 | 5.50 | 0.00 | 0.00 | 0.00 | — | — | — | — |

| Temp (° C.) | $H_2$ | $N_2$ | $CH_4$ | $C_2H_6$ | $C_2H_4$ | $C_3H_8$ | $C_3H_6$ | $X_{C_2H_6}$ (%) | $S_{C_2H_4}$ (%) | $Y_{C_2H_4}$ (%) | C balance (%) |
|---|---|---|---|---|---|---|---|---|---|---|---|
| | | | | | Alumina tube | | | | | | |
| 575 | 0.04 | 94.61 | 0.00 | 5.28 | 0.06 | 0.00 | 0.00 | 2.6 | 45.6 | 1.2 | 99 |
| 600 | 0.16 | 94.47 | 0.00 | 5.11 | 0.26 | 0.00 | 0.00 | 6.0 | 79.0 | 4.8 | 99 |
| 625 | 0.54 | 94.13 | 0.01 | 4.50 | 0.82 | 0.00 | 0.00 | 16.6 | 91.5 | 15.1 | 99 |
| 650 | 1.25 | 93.42 | 0.02 | 3.67 | 1.64 | 0.00 | 0.00 | 32.2 | 93.9 | 30.3 | 98 |
| 675 | 2.17 | 92.66 | 0.04 | 2.58 | 2.53 | 0.00 | 0.01 | 51.8 | 91.1 | 47.2 | 96 |
| 700 | 3.12 | 91.78 | 0.10 | 1.69 | 3.29 | 0.00 | 0.02 | 68.7 | 88.5 | 60.8 | 94 |
| bypass | 0.02 | 94.70 | 0.00 | 5.28 | 0.00 | 0.00 | 0.00 | — | — | — | — |
| | | | | | Stainless steel tube | | | | | | |
| 575 | 0.11 | 95.52 | 0.00 | 4.35 | 0.02 | 0.00 | 0.00 | 2.5 | 13.5 | 0.3 | 98 |
| 600 | 0.13 | 95.38 | 0.00 | 4.44 | 0.04 | 0.00 | 0.00 | 4.0 | 23.2 | 0.9 | 97 |
| 625 | 0.22 | 95.18 | 0.00 | 4.44 | 0.15 | 0.00 | 0.00 | 5.3 | 62.3 | 3.3 | 98 |
| 650 | 0.50 | 95.00 | 0.01 | 3.99 | 0.51 | 0.00 | 0.00 | 13.1 | 84.5 | 11.0 | 98 |
| 675 | 1.15 | 94.19 | 0.02 | 3.38 | 1.26 | 0.00 | 0.00 | 29.0 | 91.3 | 26.5 | 98 |
| 700 | 2.18 | 93.31 | 0.04 | 2.30 | 2.16 | 0.00 | 0.01 | 51.1 | 89.9 | 45.9 | 96 |
| bypass | 0.02 | 95.02 | 0.00 | 4.96 | 0.00 | 0.00 | 0.00 | — | — | — | — | colder than the quartz tube walls until the furnace temperature and reaction duration increased. Addition of an Inconel wire lowered ethane conversion without significant change to ethylene selectivity, as compared to the open quartz tube. This effect is similar to, but less pronounced, than that of the open stainless-steel tube, which further suggests that heat transfer affects the thermochemical reaction of ethane due to the altered conductivity of metallic components in comparison to ceramic materials, such as quartz.

Figure 2E:
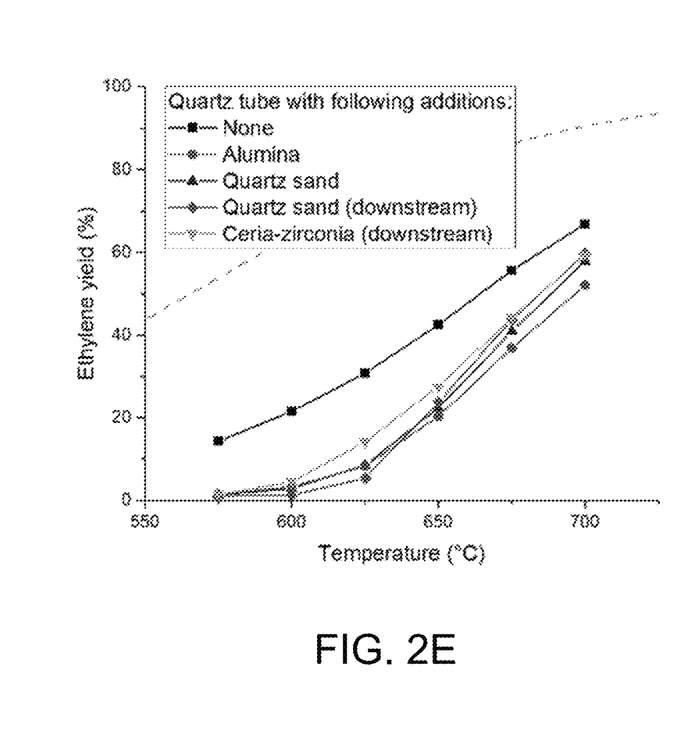
FIG. 2E is a graph of ethylene yield as a function of temperature for 5% ethane in nitrogen gas fed into quartz tube reactors with packed beds of inert material.
Figure 2F:
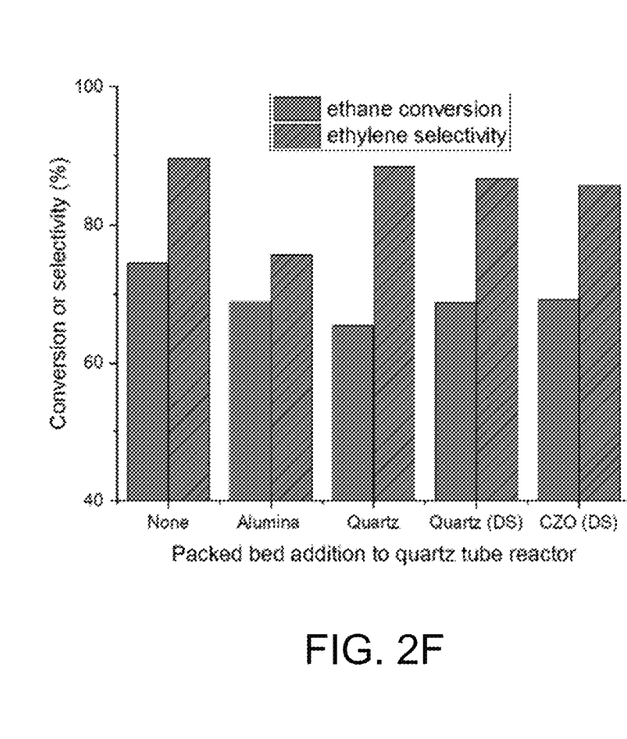
FIG. 2F is graph of ethylene selectivity and ethane conversions at a temperature of 700° C. for the inert material packed bed tube reactors.

Next, packed beds containing 20 mg of quartz sand, alumina powder, and ceria-zirconia powder were added to the quartz tube reactor. Where specified, the beds were placed downstream of the heated region of the reactor. Otherwise, the beds were positioned in the hottest region. All were supported by a quartz wool plug placed downstream of the bed. These materials are catalytically inert, however, their addition provides significantly more surface area within the reactor, which may be beneficial if the reaction was surface catalyzed. Results of the packed bed reactor experiments are shown in FIGS. 2E and 2F and Table 4.

As shown in Table 4, addition of each inert material actually had a detrimental effect on ethylene yield over the entire temperature range tested. Ethane conversion was consistently lower with the addition of a packed bed to an empty tube. Selectivity was also reduced in the presence of alumina powder due in part to higher methane production. Although an annular quartz rod had little effect on reactor performance at high temperatures, addition of quartz sand lowered performance. The open quartz tube provided an ethane conversion of 74.5% at a set furnace temperature of 700° C., which decreased to 68.7% when quartz sand was added downstream of the reactor and to 65.4% when quartz sand was added to the hottest region of the reactor. Addition of these packed bed materials likely alters flow characteristics from open tube and annular configurations. Further, powder addition significantly increases the area of solid surface which may help quench free radical reactions, limiting the extent of ethane conversion. The added solid also changes the void volume in the open tube reactor. An estimated 8 mg of quartz wool was added to retain the packed bed. At a nominal bulk density of 1 g/cc, the occupied volume is 0.028 ml. The volume of the quartz reactor is 3.19 ml, hence the added solids have very minimal impact on the residence time of the gas. However, since the added solid is located in the hottest region of the reactor, it leads to lowering the heated volume for thermal reactions.

TABLE 4

Gaseous products (measured in mole percent), ethane conversion, ethylene yield, and carbon balance as a function of temperature from reaction of 5% ethane feed gas in a quartz reactor packed with inert powders.

| Temp (° C.) | $H_2$ | $N_2$ | $CH_4$ | $C_2H_6$ | $C_2H_4$ | $C_3H_8$ | $C_3H_6$ | $X_{C_2H_6}$ (%) | $S_{C_2H_4}$ (%) | $Y_{C_2H_4}$ (%) | C balance (%) |
|---|---|---|---|---|---|---|---|---|---|---|---|
| Inconel wire in quartz tube reactor |
| 575 | 0.01 | 94.76 | 0.00 | 5.14 | 0.09 | 0.00 | 0.00 | 2.7 | 61.7 | 1.6 | 99 |
| 600 | 0.05 | 94.43 | 0.00 | 5.33 | 0.19 | 0.00 | 0.00 | 4.8 | 71.2 | 3.4 | 99 |
| 625 | 0.22 | 94.12 | 0.00 | 5.08 | 0.58 | 0.00 | 0.00 | 11.7 | 85.8 | 10.0 | 98 |
| 650 | 0.71 | 93.60 | 0.01 | 4.28 | 1.39 | 0.00 | 0.00 | 25.3 | 95.8 | 24.2 | 99 |
| 675 | 1.57 | 92.98 | 0.03 | 3.01 | 2.40 | 0.00 | 0.01 | 46.0 | 93.7 | 43.1 | 98 |
| 700 | 2.59 | 92.07 | 0.08 | 1.92 | 3.32 | 0.00 | 0.02 | 65.4 | 91.7 | 60.0 | 96 |
| bypass | 0.02 | 94.35 | 0.00 | 5.63 | 0.00 | 0.00 | 0.00 | — | — | — | — |
| Quartz sand (within heated region) |
| 575 | 0.02 | 94.89 | 0.00 | 5.03 | 0.07 | 0.00 | 0.00 | 5.7 | 22.2 | 1.3 | 96 |
| 600 | 0.05 | 94.55 | 0.00 | 5.23 | 0.16 | 0.00 | 0.00 | 8.2 | 35.4 | 2.9 | 95 |
| 625 | 0.21 | 94.27 | 0.00 | 5.02 | 0.49 | 0.00 | 0.00 | 13.2 | 64.3 | 8.5 | 95 |
| 650 | 0.64 | 93.84 | 0.01 | 4.22 | 1.28 | 0.00 | 0.00 | 22.3 | 84.1 | 22.3 | 96 |
| 675 | 1.45 | 93.05 | 0.03 | 3.09 | 2.36 | 0.00 | 0.01 | 41.0 | 88.5 | 41.0 | 95 |
| 700 | 2.40 | 91.99 | 0.08 | 2.06 | 3.45 | 0.00 | 0.02 | 57.9 | 88.4 | 57.9 | 94 |
| bypass | 0.02 | 94.47 | 0.00 | 5.51 | 0.00 | 0.00 | 0.00 | — | — | — | — |
| Quartz sand (downstream of heated region) |
| 575 | 0.01 | 94.72 | 0.00 | 5.22 | 0.06 | 0.00 | 0.00 | 5.3 | 20.2 | 1.1 | 96 |
| 600 | 0.01 | 94.46 | 0.00 | 5.45 | 0.08 | 0.00 | 0.00 | 10.3 | 12.4 | 1.3 | 91 |
| 625 | 0.03 | 94.29 | 0.01 | 5.35 | 0.32 | 0.00 | 0.00 | 10.4 | 51.3 | 5.3 | 95 |
| 650 | 0.55 | 93.88 | 0.01 | 4.18 | 1.38 | 0.00 | 0.00 | 28.2 | 84.2 | 23.7 | 96 |
| 675 | 1.45 | 93.11 | 0.04 | 2.89 | 2.50 | 0.00 | 0.01 | 49.6 | 88.2 | 43.7 | 95 |
| 700 | 2.54 | 92.09 | 0.09 | 1.81 | 3.45 | 0.00 | 0.02 | 68.7 | 86.7 | 59.6 | 93 |
| bypass | 0.02 | 94.48 | 0.00 | 5.51 | 0.00 | 0.00 | 0.00 | — | — | — | — |
| Ceria-zirconia (downstream of heated region) |
| 575 | 0.02 | 94.68 | 0.00 | 5.22 | 0.08 | 0.00 | 0.00 | 4.8 | 28.5 | 1.4 | 97 |
| 600 | 0.09 | 94.45 | 0.00 | 5.21 | 0.26 | 0.00 | 0.00 | 8.5 | 52.8 | 4.5 | 96 |
| 625 | 0.42 | 94.01 | 0.01 | 4.75 | 0.82 | 0.00 | 0.00 | 18.1 | 77.9 | 14.1 | 96 |
| 650 | 0.97 | 93.44 | 0.02 | 3.97 | 1.61 | 0.00 | 0.00 | 31.8 | 86.6 | 27.6 | 96 |
| 675 | 1.81 | 92.71 | 0.04 | 2.89 | 2.55 | 0.00 | 0.00 | 49.7 | 88.9 | 44.2 | 95 |
| 700 | 2.78 | 91.76 | 0.11 | 1.83 | 3.51 | 0.00 | 0.02 | 69.1 | 85.8 | 59.3 | 92 |
| bypass | 0.02 | 94.28 | 0.00 | 5.71 | 0.00 | 0.00 | 0.00 | — | — | — | — |
| Alumina (within heated region) |
| 575 | 0.05 | 94.15 | 0.00 | 5.70 | 0.09 | 0.00 | 0.00 | 6.7 | 22.5 | 1.5 | 95 |
| 600 | 0.13 | 93.90 | 0.01 | 5.75 | 0.21 | 0.00 | 0.00 | 8.9 | 36.8 | 3.3 | 95 |
| 625 | 0.40 | 93.61 | 0.03 | 5.44 | 0.53 | 0.00 | 0.00 | 14.1 | 58.7 | 8.3 | 95 |

TABLE 4-continued

Gaseous products (measured in mole percent), ethane conversion, ethylene yield, and carbon balance as a function of temperature from reaction of 5% ethane feed gas in a quartz reactor packed with inert powders.

| Temp (° C.) | $H_2$ | $N_2$ | $CH_4$ | $C_2H_6$ | $C_2H_4$ | $C_3H_8$ | $C_3H_6$ | $X_{C_2H_6}$ (%) | $S_{C_2H_4}$ (%) | $Y_{C_2H_4}$ (%) | C balance (%) |
|---|---|---|---|---|---|---|---|---|---|---|---|
| 650 | 1.09 | 93.04 | 0.07 | 4.53 | 1.27 | 0.00 | 0.00 | 27.6 | 73.5 | 20.3 | 94 |
| 675 | 2.18 | 92.05 | 0.16 | 3.30 | 2.30 | 0.00 | 0.01 | 47.0 | 78.4 | 36.9 | 93 |
| 700 | 3.68 | 90.76 | 0.29 | 1.97 | 3.29 | 0.00 | 0.02 | 68.9 | 75.6 | 52.1 | 88 |
| bypass | | 94.45 | 0.00 | 5.55 | 0.00 | 0.00 | 0.00 | — | — | — | — |

Figure 2G:
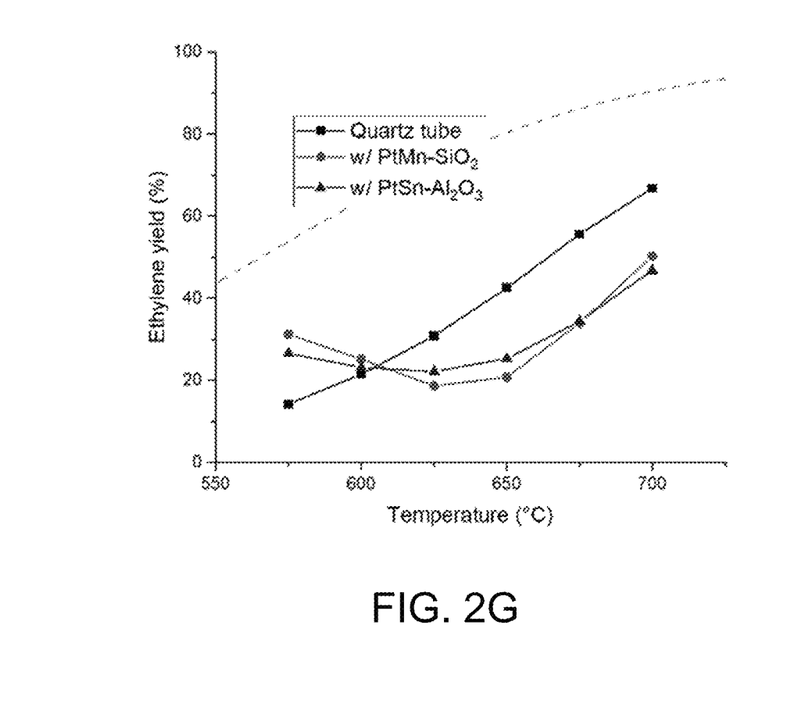
FIG. 2G is a graph of ethylene yield as a function of temperature for 5% ethane in nitrogen gas fed into quartz tube reactors with packed beds of bimetallic Pt catalysts.
Figure 2H:
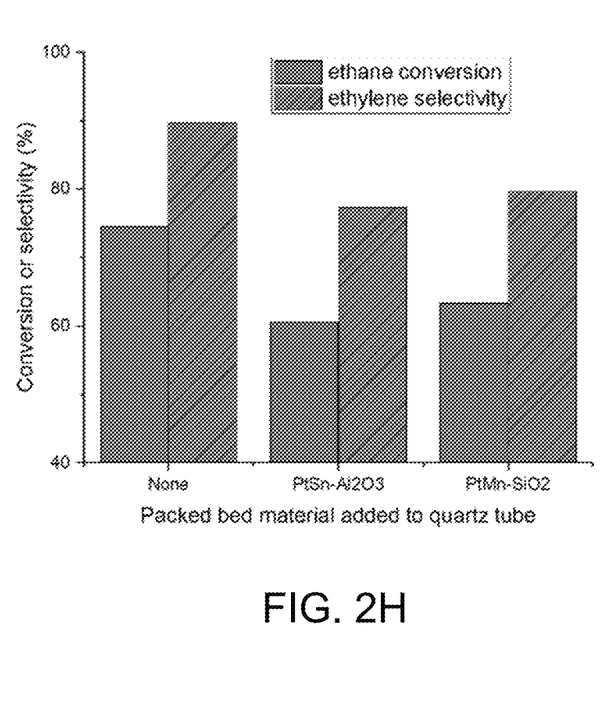
FIG. 2H is graph of ethylene selectivity and ethane conversions at a temperature of 700° C. for the catalyst packed bed tube reactors.

The addition of 20 mg packed beds of $PtMn_x$—$SiO_2$ and $PtSn_x$—$Al_2O_3$ catalysts (labeled as "PtMn" and "PtSn" for simplicity) to the quartz tube reactor was examined. Catalyst beds were always placed in the hottest region of the reactor. Results from the catalyst packed bed reactor experiments are shown in FIGS. 2G and 2H and in Table 5. The dehydrogenation performance is highly temperature dependent with these catalysts. At lower temperatures (575° C.), PtMn and PtSn catalysts increased ethane conversion to 42.5% and 35.1%, respectively, compared to 14.5% in the open tube quartz reactor. However, these catalysts degrade as temperature is increased, as evidenced by a decrease in ethylene yield as furnace temperatures increased to 625° C. Above 625° C., ethane conversion increased as thermal (as opposed to catalytic) reaction pathways became dominant. At these temperatures, ethylene yield was lower with the Pt-based catalysts than without them. In fact, better yield was achieved at 700° C. with the packed beds of alumina powder and quartz sand than with the catalysts having Pt bimetallics supported on alumina or silica. This suggests that catalytically active materials, like Pt, actually have a negative impact on the thermochemical reaction at elevated temperatures. These active surfaces may be acting as free radical quenchers. To be beneficial, the Pt-based catalysts must be operated at lower temperatures. However, ethane conversion is thermodynamically limited at low temperatures. Higher temperatures appear to deactivate these catalysts, although the catalysts tested may not have been optimized in terms of the phase and composition, and improved catalysts may lead to stable performance. The comparison of productivity between the catalytic and non-catalytic reaction needs to consider the different volume for the active region, since the heated volume of the open tube available for the thermal reaction is much greater than the volume occupied by catalyst. Hence the residence times for the gas flowing through the catalyst bed is much lower than the residence time for gas flow through an open tube. Nonetheless, these results suggest that the contribution of thermal, gas phase reactions needs to be carefully assessed when developing catalysts for ethane dehydrogenation.

TABLE 5

Gaseous products (measured in mole percent) as a function of temperature from reaction of 5% ethane feed gas in quartz tube reactors loaded with catalyst beds.

| Temp (° C.) | $H_2$ | $N_2$ | $CH_4$ | $C_2H_6$ | $C_2H_4$ | $C_3H_8$ | $C_3H_6$ | $X_{C_2H_6}$ (%) | $S_{C_2H_4}$ (%) | $Y_{C_2H_4}$ (%) | C balance (%) |
|---|---|---|---|---|---|---|---|---|---|---|---|
| $PtSn_x$—$Al_2O_3$ | | | | | | | | | | | |
| 575 | 1.58 | 93.59 | 0.06 | 3.38 | 1.38 | 0.00 | 0.00 | 35.1 | 75.7 | 26.6 | 93 |
| 600 | 1.41 | 93.63 | 0.04 | 3.71 | 1.22 | 0.00 | 0.00 | 29.3 | 78.9 | 23.2 | 95 |
| 625 | 1.40 | 93.47 | 0.04 | 3.89 | 1.20 | 0.00 | 0.01 | 28.1 | 78.8 | 22.1 | 95 |
| 650 | 1.58 | 93.32 | 0.04 | 3.66 | 1.38 | 0.00 | 0.00 | 32.9 | 77.2 | 25.4 | 93 |
| 675 | 2.06 | 92.89 | 0.07 | 3.07 | 1.90 | 0.00 | 0.01 | 44.5 | 77.3 | 34.4 | 91 |
| 700 | 2.80 | 92.24 | 0.12 | 2.21 | 2.63 | 0.00 | 0.01 | 60.6 | 77.3 | 46.8 | 89 |
| bypass | 0.02 | 94.97 | 0.00 | 5.01 | 0.00 | 0.00 | 0.00 | — | — | — | — |
| $PtMn_x$—$SiO_2$ | | | | | | | | | | | |
| 575 | 2.07 | 93.23 | 0.03 | 3.03 | 1.65 | 0.00 | 0.00 | 42.5 | 73.6 | 31.2 | 89 |
| 600 | 1.57 | 93.49 | 0.02 | 3.56 | 1.37 | 0.00 | 0.00 | 34.7 | 72.5 | 25.2 | 91 |
| 625 | 1.14 | 93.69 | 0.01 | 4.10 | 1.05 | 0.00 | 0.00 | 27.1 | 68.9 | 18.7 | 92 |
| 650 | 1.29 | 93.56 | 0.02 | 3.96 | 1.17 | 0.00 | 0.00 | 29.5 | 70.4 | 20.8 | 92 |
| 675 | 2.02 | 92.90 | 0.05 | 3.13 | 1.89 | 0.00 | 0.01 | 43.8 | 77.5 | 34.0 | 91 |
| 700 | 3.03 | 91.89 | 0.10 | 2.09 | 2.87 | 0.00 | 0.01 | 63.2 | 79.5 | 50.3 | 89 |
| bypass | 0.02 | 94.75 | 0.00 | 5.23 | 0.00 | 0.00 | 0.00 | — | — | — | — |

Figure 3A:
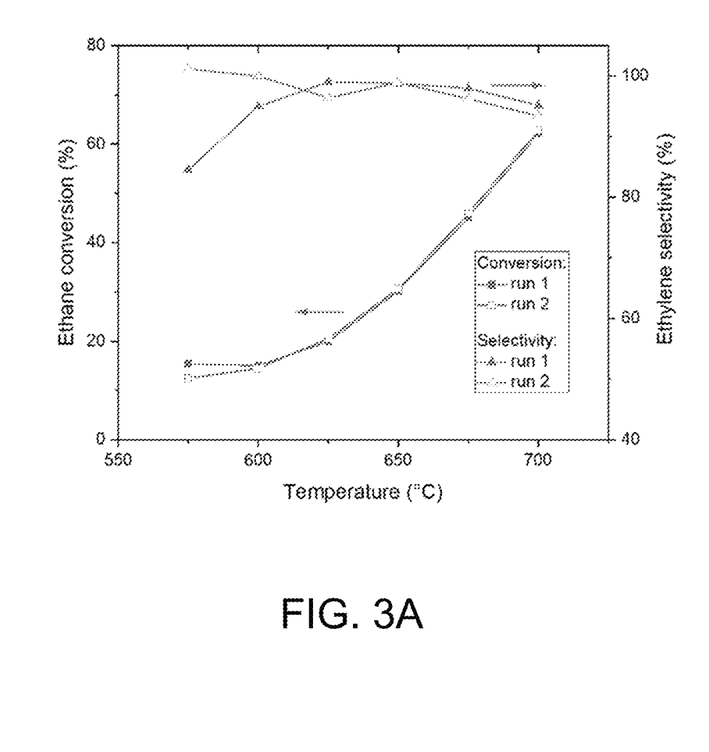
FIG. 3A shows the performance through two consecutive dehydrogenation runs using 5% ethane feed gas with a quartz open tube reactor.
Figure 3B:
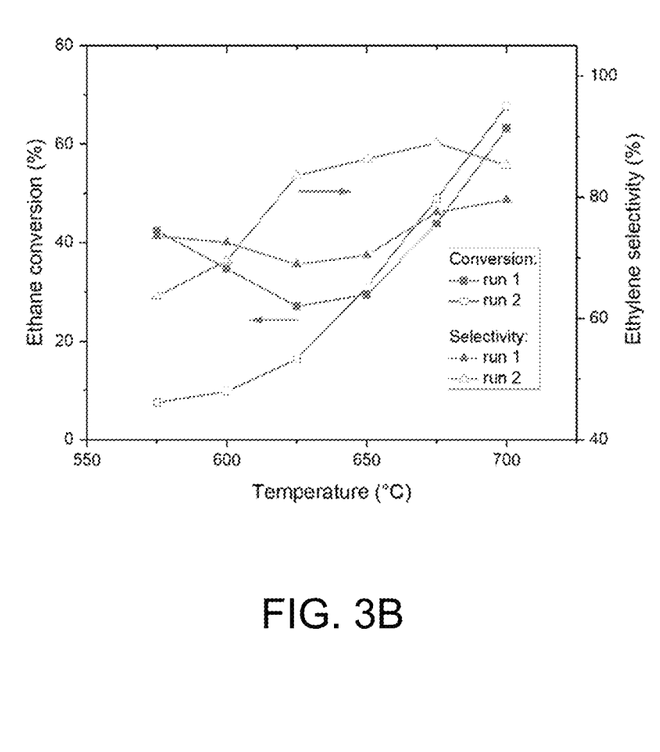
FIG. 3B shows the performance through two consecutive dehydrogenation runs using 5% ethane feed gas with a quartz tube reactor loaded with 20 mg of PtMn catalyst.

A comparison of performance stability between the catalyzed and non-catalyzed reactor configurations was evaluated by running consecutive reactions using the quartz tube with and without a packed bed of PtMn catalyst. The reaction was run as previously described, while heating from 575° C. to 700° C. The reactor was cooled to room temperature in flowing nitrogen before performing a second run without any regeneration. The results are shown in FIGS. 3A and 3B. The high conversion seen from the PtMn catalyst at low temperature was not seen in the second run. On the other hand, the quartz tube reactor showed stable performance between consecutive runs. TEM analysis of PtMn catalyst in as-prepared and post-reaction (spent) conditions was conducted to determine the cause of deactivation. The high temperatures and reducing conditions generated during non-oxidative dehydrogenation are expected to cause Pt particle sintering. While some sintering of the PtMn did occur, this effect was surprisingly minor, owing to the stability imparted through Mn alloying detailed by Wu et al. See Z. Wu et al., *J. Am. Chem. Soc.* 140, 14870 (2018). Mean particle diameter rose from 1.6 to 2.1 nm during the reaction, which is not expected to cause catalyst deactivation.

Figure 4A:
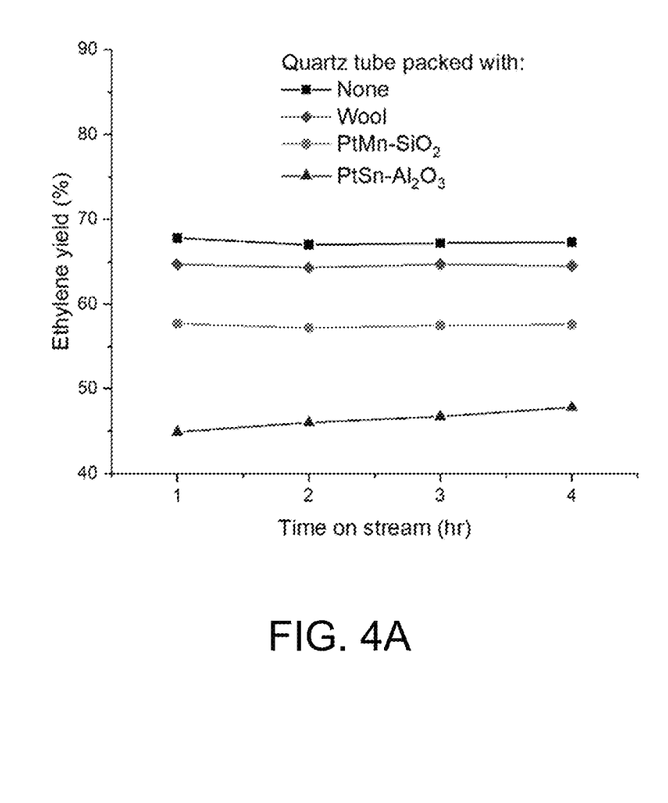
FIG. 4A is a graph of the ethylene yield of a quartz tube reactor with and without addition of quartz wool and Pt-based catalysts held at a furnace temperature of 700° C.
Figure 4B:
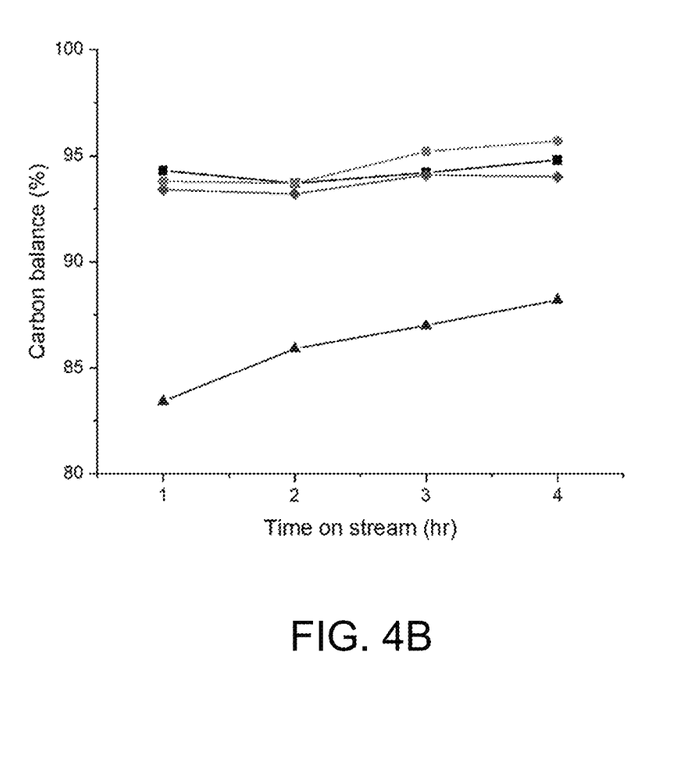
FIG. 4B is a graph of the carbon balance.
Figure 4C:
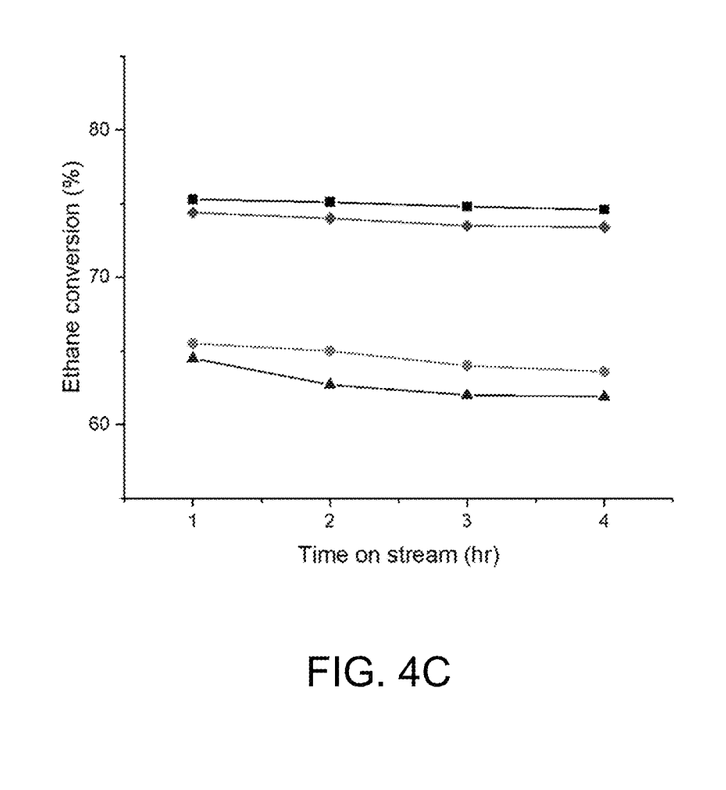
FIG. 4C is a graph of the ethane conversion.
Figure 4D:
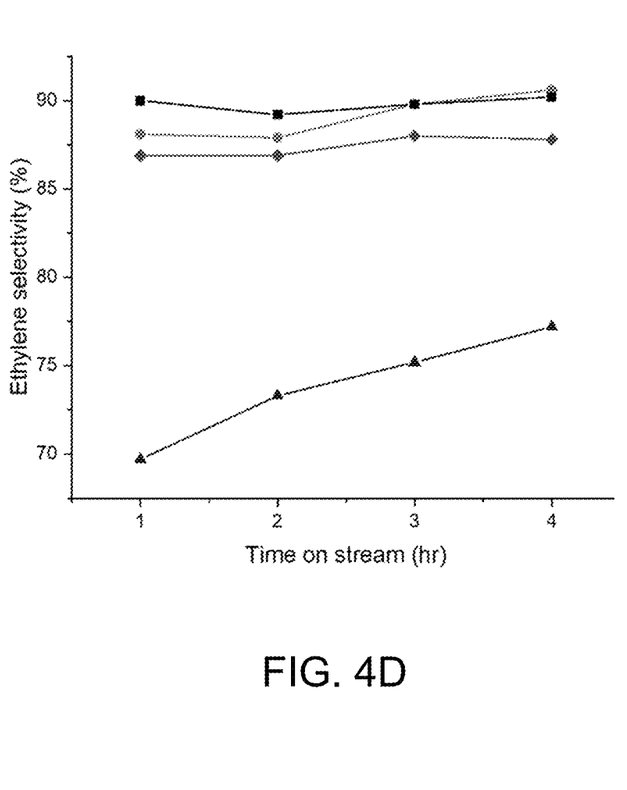
FIG. 4D is a graph of the ethylene selectivity.

An additional stability test was performed by adding 20 mg of fresh PtMn and PtSn catalysts to the quartz tube reactor, beginning the reaction at 700° C., and maintaining this temperature for 4 hours. This test was also performed with the open quartz tube alone and the quartz tube with a quartz wool plug added in the same position as used with packed catalyst beds. Results show steady performance from each reactor configuration in terms of yield, conversion, and selectivity, as shown in FIGS. 4A, 4C, and 4D. At this high temperature, the thermal reaction dominates. Addition of both catalytic and inert materials lowered ethylene yield. Carbon mole balances were calculated by summing the moles of carbon entering and exiting the reactor and correcting for the change in total moles of gas entering and exiting the reactor. As shown in FIG. 4B, carbon balances were relatively similar between each configuration with values near 95% with the exception of the $PtSn_x$—$Al_2O_3$ catalyst, which exhibited carbon balance values notably less, near 85%. Experimental limitations in quantifying all the products using the TCD and FID due to low ethane concentrations may contribute to the imperfect carbon balance, since no coke formation was detected with the open quartz tube. Coke deposits were observed on the quartz wool and on both catalysts following the reaction. Carbon analysis yielded 2.5 and 16.4 wt % carbon on spent PtMn and PtSn catalysts, respectively. Therefore, coke deposition appears to be a significant cause of Pt catalyst deactivation. Further, this observation implies that material additions to the quartz tube reactor could serve as nucleation sites for coke formation. On the other hand, smooth quartz surfaces free from defects appear to minimize coke formation. To test this hypothesis, the inner walls of a quartz open tube reactor were scratched with a stainless-steel wire. Examination of the tube following reaction showed clear signs of carbon deposits. Likewise, a tube that had been used multiple times to support a packed bed showed some carbon deposits on the wall, while a pristine quartz tube showed none. Thus, reactor wall surface roughness may be an important factor which influences carbon deposition during ethane dehydrogenation.

Figure 5A:
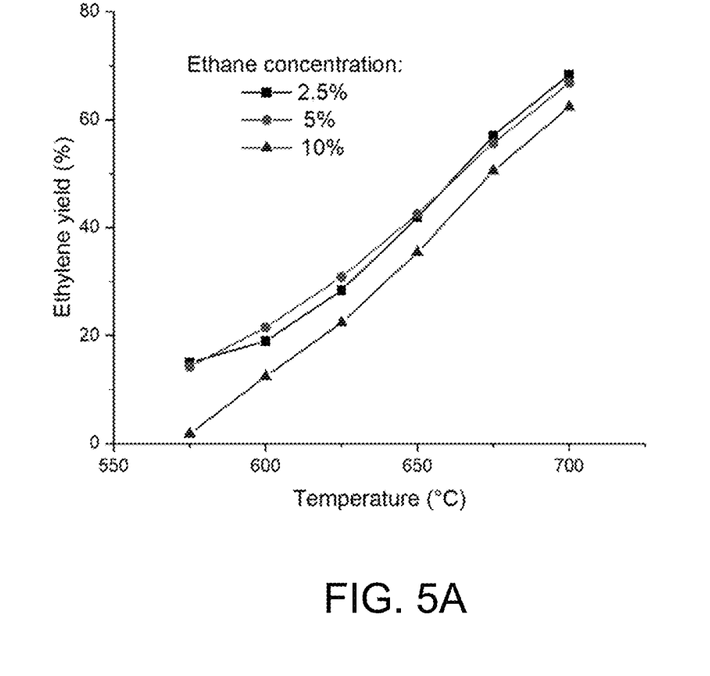
FIG. 5A is a graph of ethylene yield using a quartz open tube reactor with varying concentration of ethane feed gas.
Figure 5B:
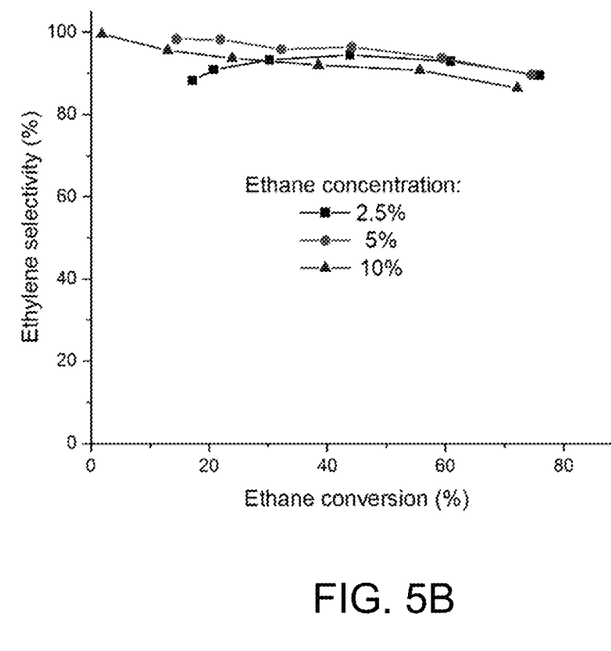
FIG. 5B is a graph of ethylene selectivity as a function of ethane conversion.

The effect of ethane concentration in feed gas was evaluated while testing the quartz open tube reactor between 575-700° C. with 2.5, 5, 10, and 25% ethane in nitrogen while keeping the $N_2$ flow rate unchanged. At a furnace set temperature of 700° C. in the quartz tube reactor, the ethylene formation rate increases linearly with ethane partial pressure, suggesting the reaction is first order with respect to ethane. Sundaram et al. similarly found the ethane thermal cracking reaction to be first order. See K. M. Sundaram et al., *AIChE J.* 27(6), 946 (1981). Ethane conversion decreased with higher ethane concentrations, while ethylene selectivity varied only between 86.4-89.5% at 700° C. among the different ethane concentrations, as shown in shown in FIGS. 5A and 5B. Likewise, selectivity only varied by several percent among the different ethane concentrations when compared at different reactor temperatures but at similar conversions. These results demonstrate the benefit of quartz tube reactors, which show robust dehydrogenation performance when operating for repeated cycles and with variation in feed gas composition.

Significant effort has been dedicated toward the development of catalysts which can withstand demanding conditions involved in ethane dehydrogenation. Often these studies do not distinguish the roles of the catalytic and thermal reactions, which become obscured at high reaction temperatures. Particularly in non-oxidative dehydrogenation studies, dehydrogenation activity may be mistakenly ascribed to the catalyst, whereas thermally induced free radical reactions are actually the dominant pathway. As described herein, high ethylene yield and selectivity can be achieved thermally with a simple open tube reactor. Introduction of both catalytic and inert materials into the heated reactor region was detrimental to the thermal reaction, resulting in lowered yield. Open tube reactors have been studied in the past, usually in the context of the oxidative coupling of methane. In their study of the OCM reaction, Keller and Bhasin found that a stainless-steel tube reactor led primarily to the formation of $CO_2$, but that a quartz tube was completely inert at temperatures ranging from 700° C. to 960° C. See G. E. Keller and M. M. Bhasin, *J. Catal.* 73, 9 (1982). Taniewski et al. demonstrated the stability of ethylene in a silica tube reactor at 700° C. and a lower tendency toward coke formation compared to stainless steel reactors. See M. Taniewski et al., *Catal. Today* 13, 529 (1992). Xu et al. achieved an ethylene yield of 56% with 61.7% conversion and 90.8% selectivity when using an open quartz tube reactor with 50% ethane feed gas. See C. Xu et al., *J. Phys. Chem. A* 115, 10470 (2011).

The present invention has been described as efficient, low-temperature, catalyst-free dehydrogenation of alkanes in a tube reactor. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for dehydrogenation of an alkane, comprising providing a tube reactor comprising
   an open quartz tube devoid of any catalyst, and
   a furnace to heat the open quartz tube;
   heating the open quartz tube to a reactor temperature of between 575° C. and 750° C.; and
   introducing a feed gas comprising an alkane into the heated open quartz tube, whereby the alkane is at least partially converted into an alkene.

2. The method of claim 1, wherein the alkane comprises ethane or propane.

3. The method of claim 1, wherein the feed gas comprises 2.5 to 25% ethane in nitrogen.

4. The method of claim 1, wherein the open quartz tube comprises a circular cross-section.

5. The method of claim 1, wherein an interior surface of the open quartz tube is smooth.

6. The method of claim 1, wherein the open quartz tube further comprises an axial rod or wire within the open quartz tube.

* * * * *